United States Patent [19]

Inacker et al.

[11] 4,303,512
[45] Dec. 1, 1981

[54] APPARATUS FOR INDICATING THE LOADING ON AN ION EXCHANGER WITH RESPECT TO A SPECIFIC METAL OR GROUP OF METALS

[75] Inventors: Otto Inacker, Immenstaad; Berthold Sessler, Würzburg, both of Fed. Rep. of Germany

[73] Assignee: Dornier-System GmbH, Friedrichshafen, Fed. Rep. of Germany

[21] Appl. No.: 163,885

[22] Filed: Jun. 27, 1980

[30] Foreign Application Priority Data

Jul. 12, 1979 [DE] Fed. Rep. of Germany ....... 2928123

[51] Int. Cl.³ .............................................. B01J 47/14
[52] U.S. Cl. ....................................... 210/93; 210/95; 210/96.1; 210/662
[58] Field of Search .......................... 204/1 T, 195 R; 210/662, 93–95, 96.1

[56] References Cited

U.S. PATENT DOCUMENTS

| 2,414,411 | 1/1947 | Marks | 210/96.1 |
| 3,400,575 | 9/1968 | Madden | 210/94 |
| 3,839,162 | 10/1974 | Ammer | 210/662 |
| 3,932,279 | 1/1976 | Yocum | 210/96.1 |
| 3,964,999 | 6/1976 | Chisdes | 210/662 |

*Primary Examiner*—Ivars C. Cintins
*Attorney, Agent, or Firm*—Marianne Rich

[57] ABSTRACT

At least part of the effluent from an ion exchanger flows past a first and second electrode. The electrodes are mounted within the pipe carrying the fluid so that they are visible from the outside. A DC voltage is applied between the electrodes. If the effluent contains a metal which should have been adsorbed by the ion exchanger, its presence is indicated either by a change in the voltage-current curve of the electrodes or a change in color of the cathode. Either a single metal or a group of metals may be precipitated.

9 Claims, 3 Drawing Figures

Viewing Direction →

APPARATUS FOR INDICATING THE LOADING ON AN ION EXCHANGER WITH RESPECT TO A SPECIFIC METAL OR GROUP OF METALS

The present application relates to ion exchanger and, more particularly, to apparatus for indicating the state of loading or saturation of an ion exchanger with respect to a particular metal or group of metals.

In known apparatus of this type, physical measurements were used such as pH measurement, electrical conductivity measurement, etc.) which, however, at best can indicate the runout of ions at the outlet. Also, indicator resins were used which also react to the pH changes of the resin and indicate the complete runout of $H^+$ ions for cation exchanges or $OH^-$ ions for anion exchanges.

These systems cannot indicate the particular type of ions against which the $H^+/OH^-$ ions were exchanged.

A system for the recovery of metal from the rinsing water of electroplating equipment is described in German published application No. P 26 02 232. In this system, at least two portable ion exchanger containers are arranged one on top of the other, a filter preceding the first; the direction of flow is from an inlet at the bottom to an outlet at the top. Both the inlet and the outlet are covered by a strainer and the edges of the containers are provided with seals. For operation of ion exchangers of this type, it is necessary that the runout of particular ions from the individual containers be determined so that a conclusion regarding the degree of saturation of the resin can be reached. The previously known methods cannot furnish the indication specific to a given metal when other elements of the same charge are present in the fluid. Further, the known methods are very expensive to implement and difficult to carry out since they require the removal of samples and analysis thereof.

SUMMARY OF THE INVENTION

It is an object of the present invention to furnish apparatus which will give indication of the saturation of a resin with respect to a specific metal or group of metals.

In accordance with the present invention, for a system wherein a stream of liquid flows through ion exchanging means in a predetermined direction, indicator apparatus is furnished which comprises a first and second electrode positioned in said liquid following said ion exchanging means in said predetermined direction and means connected to said electrodes for creating therebetween a predetermined potential difference so that said specified metal when not retained in said ion exchanging means forms a deposit on one of said electrodes.

More specifically, part of the stream of the discharge from the ion exchange container flows past the two electrodes which are visible through a window in the container holding the ion exchangers. A DC voltage applied to the electrodes causes the selected metal to be deposited on one of the electrodes when it is no longer being retained by the ion exchanger. The deposit on the electrode causes the current flowing between the anode and cathode to change. Further, if the proper cathode material is selected, the cathode can undergo a change in color due to the deposit. The selection of a particular metal or group of metals to be detected depends upon the voltage applied to the electrodes, the cathode material, and the combination of the two.

More specifically, the indicator of the present invention allows, first of all, differentiation between alkaline- and alkaline-earth metal ions on the one hand and non-ferrous and precious metal ions on the other hand. The first-named group of metal ions cannot be electrolytically separated from aqueous solutions and therefore cannot be indicated.

The second group can be separated from aqueous solutions as metals, the separation depending upon the applied voltage.

The voltage required for precipitating or depositing a metal on the electrode can be calculated from the normal electrode potential of the metal and the metal ion concentration. In general, the more precious the metal, the less the voltage required for its precipitation. Thus, by choice of the applied voltage, the most precious metal can be separated first and a specific indication of its presence can be indicated.

The required voltage can also be so chosen that a plurality of metals are simultaneously precipitated or deposited. Thus, the presence of a group of metals, for example gold and silver, or gold, silver and copper can result in an indication.

Further, the color of the deposit can be used to furnish the indication of the presence of the specific metal. Since the change in color depends upon the type, number and concentration of all simultaneously present ions, the electrode material, and the applied voltage, very complicated relationships can result. However, in practice, the stream of fluid is the rinsing water from a known process, so that the relationships are greatly simplified and the color can be used to indicate the presence of a specific metal. The actual conditions for effecting the proper color change can be determined experimentally.

It is also possible to use the current-voltage curve during the precipitation process to constitute the indication of the presence of the specific metal.

The novel features which are considered as characteristic for the invention are set forth in particular in the appended claims. The invention, itself, however, both as to its construction and its method of operation, together with additional objects and advantages thereof will best be understood from the following description of specific embodiments when read in connection with the accompanying drawing.

DESCRIPTION OF THE PREFERRED EMBODIMENT

Figure 1:
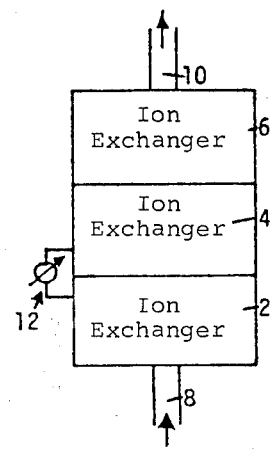
FIG. 1 is an illustration of a system requiring an indication of saturation of ion exchangers.

The known system in FIG. 1 includes a plurality of ion exchange containers 2, 4, 6 which are arranged one on top of the other. The stream of fluid flows from an inlet 8 at the bottom of the column to an outlet 10 at the top. The lower-most ion exchange container 2 should be removed when it is saturated. Upon its removal, container 4 replaces it, while ion exchange container 6 takes the place vacated by ion exchange container 4. A new ion exchange container (not shown) replaces container 6. To determine when it is necessary to remove ion exchange container 2, an indicator 12 is provided between containers 2 and 4 which indicates the state of saturation of the former.

Figure 2:
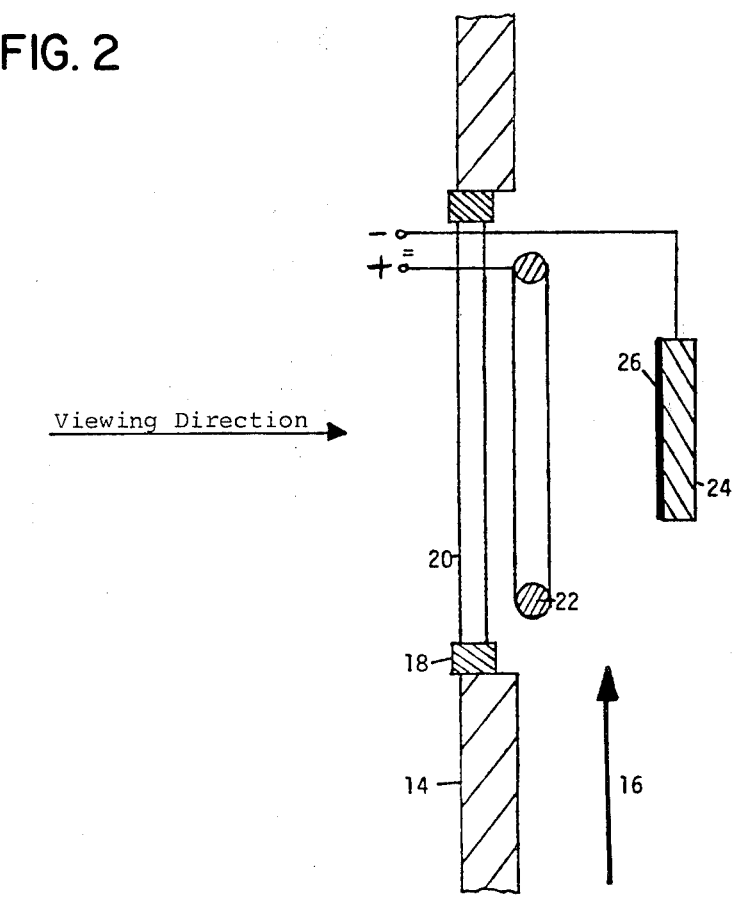
FIG. 2 is a schematic diagram illustrating the present invention.

To effect the indication, the apparatus shown in FIG. 2 is used in accordance with the present invention. Shown in FIG. 2 is a pipe 14 through which a fluid 16 flows in the direction of the arrow. A window 20 is arranged in the wall of pipe 14, seals 18 being provided. A ring-shaped anode 22 and a disk-shaped cathode 24 are located behind window 20 in the viewing direction. A potential difference is applied between the two electrodes by a DC voltage source indicated by positive and negative terminals.

If fluid 16 contains a metal, this is deposited on surface 26 of cathode 24. If the proper cathode material is chosen, surface 26 undergoes a change of color which is visible to an observer. For example, copper is a suitable cathode and anode material for an indication of the presence of gold or silver.

In experiments, a clearly visible layer of gold was deposited on a copper cathode from a gold bath having a dilution of 1 to $10^5$.

Figure 3:
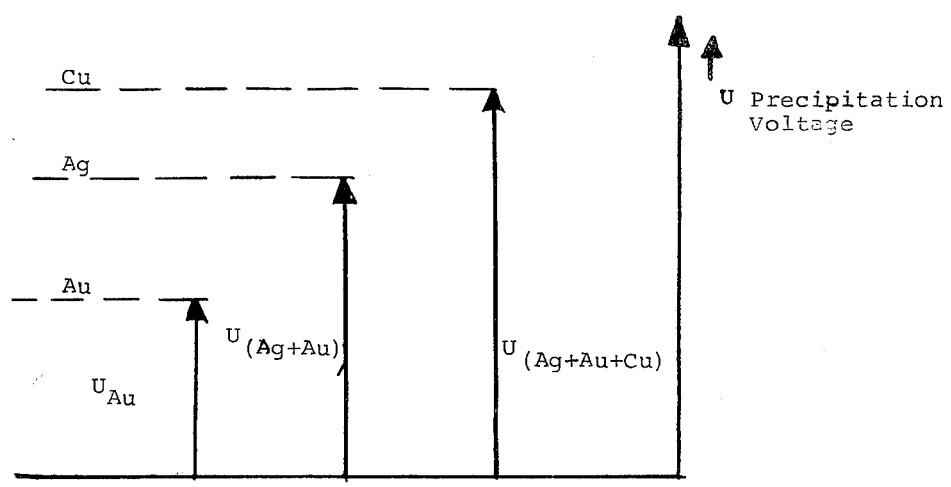
FIG. 3 is a diagram illustrating the amplitude of voltages required to separate specific metals and/or metal groups.

The relative magnitudes of voltages U for metals gold, silver and copper is shown in FIG. 3. If the voltage is very small, as indicated for $U_{Au}$, only gold is indicated. If the voltage is increased ($U_{Ag+Au}$), then the presence of both gold and silver is indicated. A further increase of voltage to $U_{(Au+Ag+Cu)}$ causes the presence of gold, silver and copper to be indicated.

Further, measurement of current and voltage can indicate whether and which metal has been deposited on the cathode. Thus examination of the voltage-current curve can also yield an indication of saturation of the ion exchanger.

While the invention has been illustrated in preferred embodiments, it is not to be limited to the circuits and structures shown, since many variations thereof will be evident to one skilled in the art and are intended to be encompassed in the present invention as set forth in the following claims.

We claim:

1. In a system comprising ion exchanging means and a stream of liquid comprising ions of at least one specified metal flowing in a predetermined direction through said ion exchanging means, apparatus for furnishing an indication of the complete loading of state of saturation of said ion exchanging means with respect to said specific metal, comprising
    a first and second electrode positioned in said liquid following said ion exchanging means in said predetermined direction; and
    means connected to said electrodes for creating therebetween a predetermined potential differnce so that said specified metal when not retained in said ion exchanging means forms a deposit on one of said electrodes.

2. A system as set forth in claim 1, further comprising a pipe carrying said stream of liquid flowing past said first and second electrodes, said pipe having a window, said first and second electrodes being mounted in said pipe so that said
    one electrode is viewable through said window.

3. A system as set forth in claim 1, wherein buildup of said deposit causes a change in electric current between said first and second electrodes;
    further comprising means for furnishing an optical indication of said electric current change.

4. A system as set forth in claim 1, wherein said first electrode is a ring-shaped anode and said second electrode is a disk-shaped cathode.

5. A system as set forth in claim 4, wherein said one electrode is said cathode.

6. A system as set forth in claim 5, wherein said deposit forms on a predetermined surface of said cathode; and
    wherein said predetermined surface is arranged in a direction parallel to said ring-shaped anode opposite the central portion thereof.

7. A system as set forth in claim 1, wherein said ion exchanging means comprises a first ion exchanger container holding a first ion exchanger;
    further comprising a second ion exchanger container holding a second ion exchanger positioned following said first ion exchange container; and
    wherein said apparatus furnishes an indication of the state of saturation of said first ion exchanger, whereby said first ion exchanger may be replaced when saturated.

8. A system as set forth in claim 1, wherein said at least one specified metal comprises a plurality of metals having electrochemical potentials different from one another, whereby forming of said deposit on said one of said electrodes by a predetermined one of said plurality of metals requires creation of a specified potential difference exceeding said predetermined potential difference for the others of said plurality of metals; and
    wherein said means for creating a predetermined potential difference creates a potential difference at least equal to said specified potential difference between said electrodes, so that said plurality of metals jointly forms a deposit on said one of said electrodes.

9. A system as set forth in claim 1, wherein said deposit creates a change of color of said one of said electrodes.

* * * * *